US007232256B2

(12) United States Patent
McGovern et al.

(10) Patent No.: US 7,232,256 B2
(45) Date of Patent: Jun. 19, 2007

(54) INTRAORAL RADIOGRAPHIC DENTAL X-RAY PACKETS HAVING NON-LEAD RADIATION SHIELDING

(75) Inventors: Michael R. McGovern, Rochester, NY (US); Kenneth J. Marshall, Brockport, NY (US); Carol A. Ryan, Macedon, NY (US); David J. Steklenski, Rochester, NY (US)

(73) Assignee: Carestream Healthcare, Inc., Rochester, NY (US)

( * ) Notice: Subject to any disclaimer, the term of this patent is extended or adjusted under 35 U.S.C. 154(b) by 0 days.

(21) Appl. No.: 10/734,861

(22) Filed: Dec. 12, 2003

(65) Prior Publication Data

US 2005/0129179 A1 Jun. 16, 2005

(51) Int. Cl.
*A61B 6/14* (2006.01)

(52) U.S. Cl. ........................................ 378/169; 378/168

(58) Field of Classification Search ................ 378/168, 378/169, 185, 184; 250/506.1
See application file for complete search history.

(56) References Cited

U.S. PATENT DOCUMENTS

| | | | | |
|---|---|---|---|---|
| 4,670,658 | A | | 6/1987 | Meyers |
| 4,912,740 | A | * | 3/1990 | Liese, Jr. .................... 378/169 |
| 4,922,511 | A | | 5/1990 | Gay |
| 5,077,779 | A | | 12/1991 | Steinhausen |
| 5,550,383 | A | * | 8/1996 | Haskell ................... 250/519.1 |
| 5,574,768 | A | * | 11/1996 | McLean ..................... 378/185 |
| 6,042,267 | A | | 3/2000 | Muraki et al. |
| 6,309,101 | B1 | | 10/2001 | Bacchetta et al. |
| 6,459,091 | B1 | | 10/2002 | DeMeo et al. |
| 6,474,864 | B1 | | 11/2002 | Resch et al. |
| 6,505,965 | B1 | | 1/2003 | McGovern |
| 6,579,007 | B1 | | 6/2003 | Bacchetta et al. |

FOREIGN PATENT DOCUMENTS

JP 02001083288 A * 3/2001

* cited by examiner

*Primary Examiner*—Hoon Song
(74) *Attorney, Agent, or Firm*—Susan L. Parulski

(57) ABSTRACT

An intraoral x-ray film packet, comprising: an outer envelope; a film chip disposed within the outer envelope; and a non-lead sheet disposed within the outer envelope, the non-lead sheet being comprised substantially of tin.

9 Claims, 1 Drawing Sheet

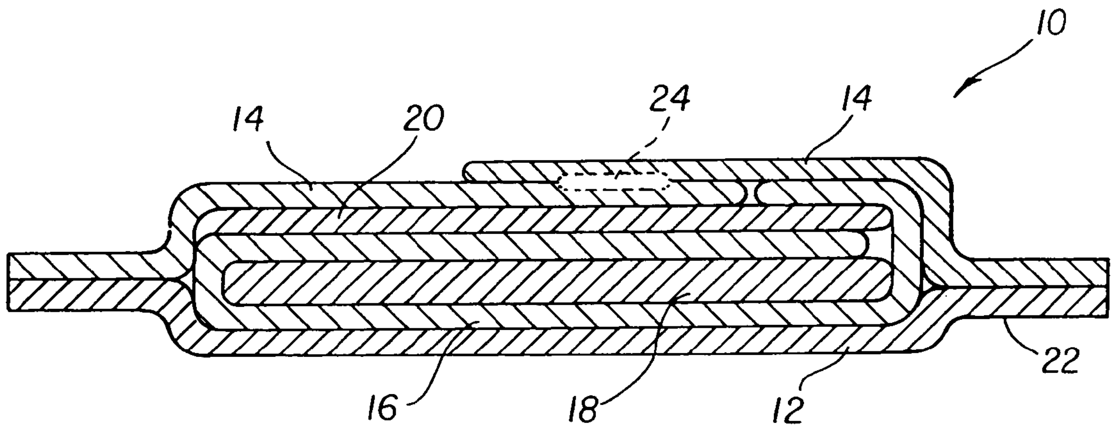
10
14
20
24
14
22
16
18
12

INTRAORAL RADIOGRAPHIC DENTAL X-RAY PACKETS HAVING NON-LEAD RADIATION SHIELDING

FIELD OF THE INVENTION

The present invention relates generally to x-ray film packets, and in particular, to intraoral radiographic x-ray film packets which do not employ lead for radiation shielding.

BACKGROUND OF THE INVENTION

Intraoral radiographic x-ray film packets, also generally referred to as intraoral radiographic film packets or dental x-ray packets have been employed in dental offices to capture x-rays of a patient's teeth and gums. Such dental x-ray packets are disclosed in U.S. Pat. No. 6,309,101 (Bacchetta), U.S. Pat. No. 6,474,864 (Resch), U.S. Pat. No. 6,505,965 (McGovern), U.S. Pat. No. 6,579,007 (Bacchetta), U.S. Pat. No. 5,077,779 (Steinhausen), U.S. Pat. No. 4,922,511 (Gay), U.S. Pat. No. 4,912,740 (Liese, Jr.) all commonly assigned and incorporated herein by reference.

It is known in the art that heavy metals provide a shielding effect against various forms of radiation. Their effectiveness is associated with the size of their atomic nucleus or as is commonly referred in the art, their absorption cross-section. An effective heavy metal used to provide the shielding function in current medical and dental radiography is lead (atomic number 82). Lead has several advantages. The ease with which it is formed, combined with its high density and relatively low cost make it a prime material to use in x-ray applications. Lead also provides high quality radiographic images by minimizing the image effects of backscattered radiation.

Yet, since certain heavy metals, like lead, are difficult to handle in certain applications and there is a perception that these heavy metals pose environmental issues, there exists an opportunity to not use lead for dental and medical radiographic applications. This opportunity exists even for applications wherein there is no patient contact with the lead, such as dental x-ray packets. Accordingly, there exists a need for a dental x-ray packet that does not employ lead for radiation shielding.

U.S. Pat. No. 6,459,091 (DeMeo) relates to a radiation protective garment having barium sulfate coated fibers. U.S. Pat. No. 4,670,658 (Meyers) is directed to a flexible sheet coated with barium sulfate that is used to shield or protect medical personnel during procedures where radiation backscatter can be a problem. While such systems may have achieved certain degrees of success in their particular applications, such materials are not suitable for shielding radiation in a dental x-ray packet because the required thickness to provide equivalent absorption would make the dental packet exceed ANSI standards and too rigid.

U.S. Pat. No. 6,042,267 (Muraki) discloses an intraoral x-ray image pickup apparatus which uses copper tungsten as an x-ray shielding member which is not suitable for the present application because of the necessary thickness to realize the same x-ray shielding effect as that of the lead member.

The present invention is directed to a dental x-ray packet which does not employ lead for radiation shielding, and such radiation shielding material is sufficiently malleable/formable so as to be incorporated into a dental x-ray packet, yet provide for comfortable operation when used by a patient, and still minimize the image effects of backscattered radiation.

SUMMARY OF THE INVENTION

An object of the present invention is to provide a dental x-ray packet that does not employ lead for radiation shielding.

Another object of the present invention is to provide such a dental x-ray packet that provides comfortable operation when used by a patient.

A further object of the present invention is to provide such a dental x-ray packet that provides high quality radiographic images.

Yet another object of the present invention is to provide such a dental x-ray packet that employs a material that is not perceived to have environmental issues.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a dental x-ray packet that employs a tin foil for radiation shielding. More particularly, according to one aspect of the present invention, there is provided an intraoral x-ray film packet comprising: an outer envelope; a film chip disposed within the outer envelope; and a non-lead sheet disposed within the outer envelope, the non-lead sheet being comprised substantially of tin. In a preferred embodiment, the non-lead sheet is comprised of at least 99.95 percent tin, preferably about 99.975 percent tin. In a further preferred embodiment, the non-lead sheet is a tin foil having a thickness of about 0.002 to about 0.0024 inches.

BRIEF DESCRIPTION OF THE DRAWINGS

The foregoing and other objects, features, and advantages of the invention will be apparent from the following more particular description of the preferred embodiments of the invention, as illustrated in the accompanying drawings.

FIG. 1 shows a cross-sectional view of a dental film packet in accordance with the present invention.

DETAILED DESCRIPTION OF THE INVENTION

The following is a detailed description of the preferred embodiments of the invention, reference being made to the drawings in which the same reference numerals identify the same elements of structure in each of the several figures.

Typically, lead foil (which is an alloy of lead with about 1.5% tin and about 2.5% antimony) is currently used in direct dental radiography for radiation shielding.

The present invention relates to the use of thin non-lead metal foils as a means to shield radiation in the construction of intraoral radiographic x-ray dental packets.

FIG. 1 shows a cross-section of a dental x-ray packet 10 in accordance with the present invention. Dental x-ray packet 10 includes an outer envelope comprising a first sheet 12 on one face of packet 10 and a pair of overlapping sheets 14 on the opposite face thereof. Contained within sheets 12 and 14 is a paper wrapped element 16, a film chip 18, and radiation shielding member 20. In the embodiment shown in FIG. 1, sheets 12 and 14 project beyond dimensions of paper wrap element 16, film chip 18, and radiation shielding member 20 to yield a laminated perimetric edge 22. Laminated perimetric edge 22 allows for heat sealing of sheets 12 and 14 to one another to yield a light tight perimeter to packet 10. A heat seal 24 can be generated at the overlap of sheets 14 to provide an outer envelope which is completely light-tight.

Sheets 12 and 14 can be comprised of vinyl or a soft thermoplastic material such as, but not limited to, polyvinyl chloride (PVC) or ethylene vinyl acetate (EVA).

Radiation shielding member 20 is not comprised of lead. Rather radiation shielding member 20 is comprised of tin (atomic symbol Sn) sufficient to absorb backscattered radiation in at oral x-ray energies from about 60 to about 80 kVp, where kVp stands for peak kilovoltage and represents the accelerating voltage of the x-ray generator and is a measure of the peak energy of the x-ray photon. More particularly, radiation-shielding member 20 is a metallic tin foil comprised of greater than 98 percent tin, preferably at least 99.95 percent tin, preferably about 99.975 percent tin.

With such a configuration of tin, a pure tin foil of thickness 0.0024+/−0.0002 inches (i.e., about 0.0022 to about 0.0026 inches) would absorb at about the same amount of 60 kVp to about 80 kVp x-ray photons at a thickness of about 0.002 inches of lead.

Applicants have recognized advantages of using tin over any other non-lead metals. Table 1 shows the calculated thickness in inches of several common metallic foils which would be needed to absorb the same percentage of 60 and 80 kVp x-ray photons as absorbed by the currently used 0.002 inches of lead foil.

TABLE 1

| Metal | 80 kVp Equivalent thickness | 60 kVp Equivalent thickness |
|---|---|---|
| Al | 0.1008 | 0.1520 |
| Mg | 0.1618 | 0.2549 |
| Ti | 0.0298 | 0.0328 |
| Fe | 0.0117 | 0.0120 |
| Cu | 0.0080 | 0.0080 |
| Zn | 0.0092 | 0.0091 |
| Ag | 0.0020 | 0.0019 |
| Sn | 0.0025 | 0.0024 |
| W | 0.0004 | 0.0016 |
| Pb | 0.0020 | 0.0020 |

Some common foils (for example, those based on aluminum, magnesium, copper, zinc, and iron) are unsuitable for Applicant's dental application because of the thickness required. At the thicknesses shown, the resulting dental packet would be difficult to manufacture (particularly employing existing equipment), would be very stiff (i.e., not flexible), and the thickness of the resulting dental packets would exceed current standards. While metallic foil based on silver might appear to be a possibility based on its thickness, there is a high cost for silver. Tungsten foil might also appear to be a suitable metallic foil for this application, however tungsten is also very expensive and tungsten foils are extremely brittle and hard to cut/form. Applicants have recognized that metallic tin foil can be purchased at a reasonable price, have a substantially equivalent thickness for equivalent absorption relationship with lead, and be amenable to use with existing manufacturing equipment. Accordingly, the dental packet based on tin foil would have approximately the same thickness as the current packet based on the lead foil, would have similar flexibility, and would have the same ability to absorb backscattered radiation.

Table 2 shows the average lead weights for Eastman Kodak Company film sizes that Applicants have recognized could be replaced with tin foil

TABLE 2

| SIZE | WEIGHT OF LEAD (Grams) |
|---|---|
| 0 | 0.52 |
| 1 | 0.65 |
| 2 | 0.88 |
| 3 | 1.04 |
| 4 | 3.20 |

The tin foil for the present invention can be produced by known manufacturing processes such as hot or cold roll forming.

Once manufactured, the tin foil can then cut to the desired size. For example, the tin foil can be purchased as a wound roll of foil and then cut into size.

The radiation shielding member of the present invention has such a thickness that radiation shielding member 20 can be substituted for the lead foil currently used within dental x-ray packets, thereby allowing existing dental x-ray packets to be retro-fitted with the radiation shielding member 20 of the present invention.

Tin is silvery, malleable and is a soft metal that is rollable into thin sheets of tin foil. Tin is located in group IVB on the periodic table, and its atomic mass is 118.710. There are two oxidation states (4 & 2). Tin melts at about 232 degrees C. and boils at about 2270 degrees C. The density 7.31 grams/cc versus 11.35 grams/cc for lead. Tin has a crystalline structure. The crystal structure is tetragonal. The ordinary form of the metal is the beta form known as white tin.

Tin foil provides an absorption cross section similar to that of lead at diagnostic x-ray energies, with similar manufacturing cost and processes, but is viewed as having fewer environmental concerns. In addition, tin does not require special handling by manufacturing workers involved in production and recycling.

Radiation shielding member 20 can be employed with other configurations of a dental x-ray packet than that shown in FIG. 1. For example, U.S. Pat. No. 6,474,864 (Resch) discloses a packet having a comfort-enhancing feature. Other configurations are shown in U.S. Pat. No. 6,309,101 (Bacchetta), U.S. Pat. No. 6,505,965 (McGovern), U.S. Pat. No. 6,579,007 (Bacchetta), U.S. Pat. No. 5,077,779 (Steinhausen), U.S. Pat. No. 4,922,511 (Gay), and U.S. Pat. No. 4,912,740 (Liese, Jr.).

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST

10 dental x-ray packet
12 sheet
14 overlapping sheet
16 paper wrap element
18 film chip
20 radiation shielding member
22 laminated perimetric edge
24 heat seal

What is claimed is:

1. An intraoral x-ray film packet, comprising:

an intraoral outer envelope;

a film chip disposed within the outer envelope; and a non-lead shielding sheet disposed within the intraoral outer envelope, the non-lead sheet being comprised substantially of tin, the non-lead sheet being comprised of at least 99.95 percent tin.

2. The intraoral x-ray film packet according to claim 1, wherein the non-lead sheet is comprised of about 99.975 percent tin.

3. The intraoral x-ray film packet according to claim 1, wherein the non-lead sheet is a tin foil having a thickness of about 0.002 to about 0.0024 inches.

4. The intraoral x-ray film packet according to claim 1, wherein the non-lead sheet absorbs between about 60 kVp to about 80 kVp of radiation energy.

5. The intraoral x-ray film packet according to claim 1, wherein the outer envelope includes a laminated perimetric edge.

6. An intraoral x-ray film packet adapted to capture an intraoral image when exposed to a source of radiation, comprising:

an intraoral outer envelope;

a film chip disposed within the intraoral outer envelope; and a non-lead shielding sheet disposed within the intraoral outer envelope adapted to absorb backscatter radiation when exposed to a source of radiation, the non-lead sheet being comprised substantially of tin, the non-lead sheet being comprised of at least 99.95 percent tin.

7. The intraoral x-ray film packet according to claim 6, wherein the non-lead sheet is disposed on one side of the film chip such that, when the film chip is exposed to a source of radiation to capture the intraoral image, the film chip is intermediate the source of radiation and non-lead shielding sheet.

8. The intraoral x-ray film packet according to claim 6, wherein the non-lead sheet is comprised of about 99.975 percent tin.

9. The intraoral x-ray film packet according to claim 6, wherein the non-lead sheet is a tin foil having a thickness of about 0.002 to about 0.0024 inches.

* * * * *